(12) United States Patent
Colin et al.

(10) Patent No.: US 11,060,053 B2
(45) Date of Patent: Jul. 13, 2021

(54) METHOD AND DEVICE FOR HYDRATING A HYDRATING MEDIUM BY A LIQUID SAMPLE

(71) Applicant: BIOMÉRIEUX, Marcy l'Étoile (FR)

(72) Inventors: Bruno Colin, Marcy l'Etoile (FR); Laurence Dévigne, Vaux en Bugey (FR); Sandrine Ghirardi, Saint Genis les Ollières (FR); Marie-Pierre Montet, Vénissieux (FR); Christine Rozand, Saint Genis les Ollières (FR); Philippe Wandels, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 633 days.

(21) Appl. No.: 15/579,648

(22) PCT Filed: Jun. 6, 2016

(86) PCT No.: PCT/FR2016/051346
§ 371 (c)(1),
(2) Date: Apr. 25, 2018

(87) PCT Pub. No.: WO2016/193647
PCT Pub. Date: Dec. 8, 2016

(65) Prior Publication Data
US 2019/0119617 A1    Apr. 25, 2019

(30) Foreign Application Priority Data
Jun. 5, 2015   (FR) ..................... 15 55145

(51) Int. Cl.
*C12M 1/32* (2006.01)
*B01L 3/00* (2006.01)
(Continued)

(52) U.S. Cl.
CPC ........... *C12M 23/12* (2013.01); *B01L 3/5025* (2013.01); *B01L 3/50853* (2013.01);
(Continued)

(58) Field of Classification Search
None
See application file for complete search history.

(56) References Cited

U.S. PATENT DOCUMENTS 8,343,726 B2    1/2013  Boone et al.
2003/0047451 A1*  3/2003  Bhullar .................. G01N 33/52
                                                        204/403.01
(Continued)

FOREIGN PATENT DOCUMENTS

EP    0 319 294 A2    6/1989
EP    1 174 716 A2    1/2002
(Continued)

OTHER PUBLICATIONS

International Search Report, dated Aug. 29, 2016, corresponding to PCT/FR2016/051346; French Search Report, dated Apr. 13, 2016, corresponding to French Application No. 1555145.

*Primary Examiner* — William H. Beisner
(74) *Attorney, Agent, or Firm* — Ladas & Parry LLP; Malcolm J. MacDonald

(57) ABSTRACT

The invention relates to a device for hydrating with a liquid sample, the device comprising a container (4) for receiving at least one liquid sample, and a lid (5) possessing a bottom face ($5_1$) having at least one hydrating support (3) fastened thereto to present an absorption face ($3_1$) for absorbing a liquid sample. According to the invention, the container (4) presents, by means of at least one well (6), a calibrated volume for receiving a liquid sample, the at least said well presenting a hydrating calibrated open section for hydrating a hydrating support (3) defined by the top edge (8) of at least said well (6), the hydrating calibrated open section possess-
(Continued)

ing an area that is less than the area of the absorption face of the hydrating support (3) in order to control the absorption by capillarity of the liquid sample by the hydrating support.

26 Claims, 8 Drawing Sheets

(51) Int. Cl.
    *C12M 1/00*     (2006.01)
    *C12Q 1/06*     (2006.01)

(52) U.S. Cl.
    CPC ............... *C12M 29/26* (2013.01); *C12Q 1/06* (2013.01); *B01L 2300/047* (2013.01); *B01L 2300/069* (2013.01); *B01L 2300/0636* (2013.01); *B01L 2300/0825* (2013.01); *B01L 2300/0829* (2013.01); *B01L 2300/0864* (2013.01); *B01L 2300/0887* (2013.01); *B01L 2400/0406* (2013.01)

(56) References Cited

U.S. PATENT DOCUMENTS

2004/0087033 A1*   5/2004   Schembri ................ B01L 3/505
    506/39
2007/0183936 A1*   8/2007   Newsam ............ G01N 33/5082
    422/400

FOREIGN PATENT DOCUMENTS

| EP | 1 415 788 A1 | 5/2004 | |
|----|---|---|---|
| EP | 1415788 A1 * | 5/2004 | .......... B01J 19/0046 |
| WO | 2005/012549 A2 | 2/2005 | |

* cited by examiner

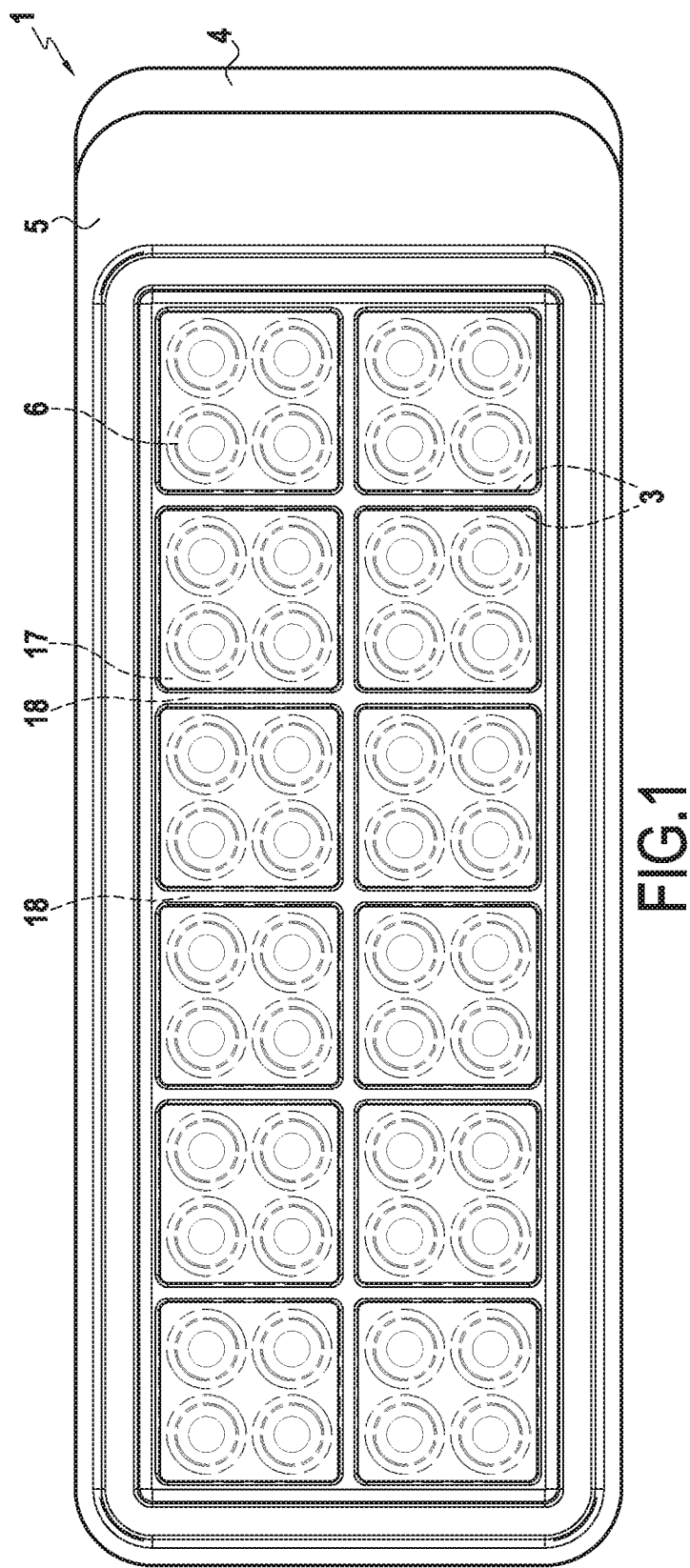
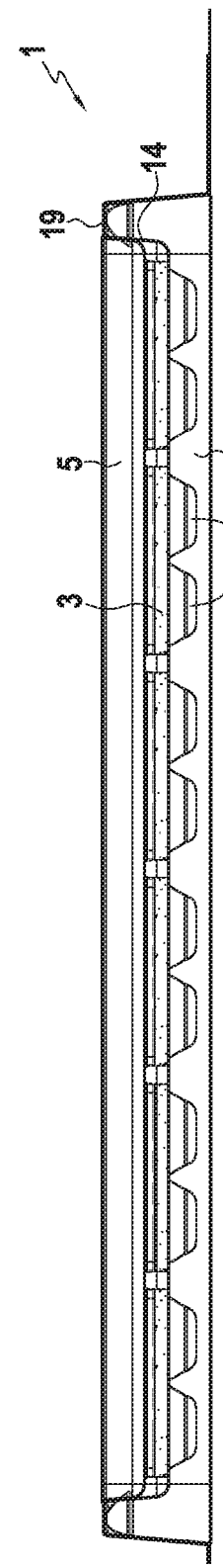
FIG. 1
FIG. 2

METHOD AND DEVICE FOR HYDRATING A HYDRATING MEDIUM BY A LIQUID SAMPLE

The present invention relates to the technical field of hydrating a hydrating support with a liquid sample, the hydrating support including a reaction medium in the general sense.

The subject matter of the invention finds advantageous applications in numerous fields in which there arises a need to use a liquid to activate a reaction medium previously incorporated in a hydrating support.

For example, the subject matter of the invention finds a particularly advantageous application in the field of hydrating supports impregnated with a reaction medium and requiring rehydration immediately prior to utilization in order to activate the reaction medium and make them ready for use.

A particularly preferred application lies in microbiological assay. It requires techniques to be implemented that make it possible to detect microorganisms—e.g. for detection purposes and/or for enumerating purposes—and for which results need to be returned as quickly as possible. In general manner, said microorganisms need not be pathogenic, e.g. bacteria of technological interest, such as fermenting agents or quality indicators; these serve to validate a production process, from raw materials or substances to finished products. Nevertheless, the microorganisms that are subjected to microbiological assay are very often pathogenic, thus requiring detection that is fast and accurate in order to undertake appropriate corrective actions as soon as possible. Naturally, the toxins produced by such pathogenic microorganisms—and responsible for all or part of their pathogenic nature—may also be looked for.

In any event, and whatever the origin of the sample being subjected to microbiological assay, the important factors for evaluating the effectiveness of the assay are: sensitivity, specificity, and time-to-result.

Thus, a particularly advantageous application of the invention is to detect and/or identify and/or enumerate at least one organism in a liquid sample that might contain it.

A preferred application of the subject matter of the invention seeks to determine the sensitivity and the resistance to at least one antibiotic of at least one microorganism that might be contained in a liquid sample.

The prior art has proposed numerous technical solutions for identifying or detecting a living organism or an analyte in a liquid sample.

Thus, patent EP 0 319 294 describes a method and a device for determining the presence of an analyte in a liquid sample. That device comprises firstly a reaction cell having a microporous membrane carried by an absorbent material, and secondly a liquid sample applicator in the form of a tube having an orifice with an open area that is substantially smaller than the area of the membrane. That device also has a reagent system comprising components capable of co-operating with the analyte held in the microporous membrane in order to produce a visual signal. The applicator is put into contact via its orifice with the membrane in order to concentrate the analyte of the sample and/or the components of the reagents in the contact area so as to produce a visual signal having the dimensions of the orifice. Although such a device enables the reaction to be concentrated in order to improve visualization, such a device is found to be difficult to implement, in particular concerning control over the transfer of the liquid sample onto the membrane and placing the reagent system so as to obtain the reaction with the analyte of the sample.

U.S. Pat. No. 8,343,726 describes a device for detecting substances present in a liquid. That device comprises firstly a container containing a porous material for receiving a liquid sample, and secondly a porous membrane impregnated with a culture medium. The porous membrane is for placing in a superposed position over the container in order to come into contact with the liquid sample that diffuses into the membrane. Such a device presents the drawback of not being able to control the hydrating of the porous membrane by the liquid sample. Unfortunately, migration of the liquid sample inside the hydrating support needs to be well controlled so as to avoid disturbing the distribution of the reaction medium in the hydrating support, since that would modify reaction conditions. Conversely, the liquid sample needs to be capable of hydrating all of the hydrating support so that it delivers its optimum reaction capacity.

On the same lines, patent application EP 1 415 788 describes a microfluidic device for chemical and biological analysis that comprises, in the embodiment of its FIG. 5, firstly a microfluidic component having wells and secondly a lid provided with substrates carrying a matrix of reagents. When the lid is placed over the microfluidic component, the substrate becomes placed in a chamber defined by the well in order to be hydrated by the liquid medium contained in the microfluidic component.

That embodiment of the microfluidic device gives no indication about capacity for controlling the hydrating of the substrate by the liquid medium. Nevertheless, in the embodiment shown in FIG. 4, the substrate carrying the matrix of reagents is positioned completely inside the well, such that hydrating of the substrate by the liquid medium is not controlled.

In the technical field of biosensors, patent application EP 1 174 716 describes a biosensor having a substrate with electrodes and presenting a liquid sample receiving well provided with a test reagent. The biosensor is provided with a lid enabling the test zone to be protected before and after use. In the embodiment shown in FIGS. 9 to 11, the lid is provided with a substrate for absorbing excess liquid. That device, which proposes pouring the liquid medium into the well, does not make it possible to control the hydrating of the substrate by the liquid medium.

In the technical field of membranes, patent application WO 2005/012549 describes apparatus for evaluating the barrier properties of a membrane. That apparatus includes a test membrane mounted between a donor plate and a receiver plate. The donor plate is arranged to include wells of liquid samples having electrodes mounted in association therewith. That apparatus, which seeks to characterize the characteristics of membranes, does not control the hydrating of the membrane by the liquid sample.

The subject matter of the invention seeks to remedy the drawbacks of the prior art by proposing a novel technique making it possible in simple and reliable manner to control the hydrating of a hydrating support by a liquid sample without generating disturbances in the reaction medium of the hydrating support and while optimizing reaction conditions for the reaction medium with the liquid sample.

To achieve this object, the invention provides a device for hydrating a hydrating support that contains a reaction medium with a liquid sample, the device comprising:
  a container for receiving at least one liquid sample, the container including at least one reception well that is upwardly open at a top edge; and a lid possessing a bottom face having at least one hydrating support fastened thereto to present an absorption face for absorbing a liquid sample when the lid and the container occupy a hydrating position in which the hydrating support is in contact with the liquid sample via a hydrating interface.

According to the invention, the container presents, by means of at least one well, a calibrated volume for receiving a liquid sample, the at least said well presenting a hydrating calibrated open section for hydrating a hydrating support defined by the top edge of at least said well, the hydrating calibrated open section possessing an area that is less than the area of the absorption face of the hydrating support in order to control the absorption by capillarity of the liquid sample by the hydrating support.

The device of the invention makes it possible firstly to measure out in simple and accurate manner the volume of liquid sample that is needed to react with all of the reaction medium of the hydrating support, and secondly to control the conditions under which the liquid sample is put into contact with the reaction medium in order to optimize activation and/or reaction conditions.

In an advantageous embodiment, the area of the calibrated open section for hydrating a hydrating support by a liquid sample defined by at least one well is such that the ratio of this area of the calibrated section for hydrating a hydrating support with a liquid sample, over the area of the absorption face of the hydrating support lies in the range 40% to 80% and preferably in the range 50% to 75%, and advantageously in the range 55% to 65%.

In a preferred variant embodiment, the container includes reception wells for a plurality of liquid samples, and the lid is fitted with a plurality of hydrating supports that are spaced apart from one another by separation corridors and each of which is to be hydrated, in the hydrating position by a respective liquid sample.

This variant embodiment makes it possible to hydrate a plurality of hydrating supports while avoiding cross-contamination between the hydrating supports and consequently between the liquid samples. The separation corridors also make it possible to cause air to flow between the hydrating supports in order to encourage growth of certain bacteria during incubation. In an embodiment, the area of the calibrated open section for hydrating a hydrating support by a liquid sample is defined by a plurality of wells, each presenting a hydrating calibrated open section, which section, in combination with the other well sections, present a total area corresponding to the area of the calibrated open section for hydrating a hydrating support. This embodiment makes it possible to distribute the contact front between the liquid sample and the surface of the hydrating support by selecting the number of wells as a function of the area of the hydrating support. Furthermore, distributing the liquid sample in a plurality of wells optimizes measuring out the liquid sample.

In another advantageous embodiment, each well includes a plurality of reception cavities for respective portions of the liquid sample, the reception cavities communicating with one another at least via the hydrating calibrated open section, which is of outline that possesses various lobes. Distributing the liquid sample in various cavities enables the liquid for analysis to be measured out better, which is important if it is somewhat viscous (as applies to milk for example or dilute liquid samples).

In another embodiment, the area of the calibrated open section of the container for a liquid sample is defined by a single well. This embodiment makes it possible to improve the visibility of the test through the device during the read step.

According to an advantageous embodiment characteristic, the container includes at least one well communicating with a feed microchannel having a portion situated outside the hydrating interface, the well and the microchannel defining a calibrated reception volume for receiving a liquid sample and presenting a hydrating calibrated open section defined by the top edge of the well and at least a portion of the top edge of the microchannel. These microchannels then enable the wells to be fed more easily with the liquid sample. After hydration, the empty microchannels serve to allow air to flow in the wells, thereby providing the advantage of limiting the effects of condensation on the bottoms of the wells so as to facilitate reading through them.

Advantageously, each well presents a hydrating calibrated open section defined by an outline that is outside the microchannels, thereby leaving a peripheral belt in the hydrating position on the absorption face of the hydrating support, which belt lies between said outline and the peripheral edge of the hydrating support. The liquid sample is thus absorbed without risk of leaks and pollution between the wells.

In a variant embodiment, the lid is provided with a plurality of hydrating supports, each of which is to be hydrated by a respective liquid sample, and in that the number and the volume of wells facing each hydrating support are identical for all of the hydrating supports. Such a variant embodiment enables a plurality of hydrating supports to be hydrated simultaneously and in identical manner, thereby making it possible to perform multiplexed detection of microorganisms.

In order to improve the conditions for transferring the liquid sample onto the hydrating support, at least one well presents a profile that tapers going away from its top edge.

According to an advantageous embodiment characteristic, the container includes a plate in which the well(s) and the microchannels are arranged so as to be surrounded by respective peripheral rim(s) that serve in the hydrating position as abutment surfaces for the hydrating supports.

In a preferred embodiment, the container includes a plate in which the well(s) is/are arranged and from which a peripheral margin surrounding the wells projects upwards defining internally at least one distribution bowl for distributing the liquid sample(s). Such a container facilitates the operation of distributing the liquid sample(s) in a single operation without risk of overflow.

When the liquid sample is transparent, each well is advantageously provided with a stain for the liquid sample in order to assist in filling said well. In a variant embodiment, the container has at least one separation partition in order to define at least two distribution bowls, each for a liquid sample that is different from one bowl to the other. In this embodiment, the device makes it possible to provide different hydrating conditions, e.g. with a liquid sample of dilution that is different, e.g. making it possible to have a reference hydrating support.

Advantageously, the lid possesses a peripheral groove suitable for engaging on the peripheral margin of the container.

In a variant embodiment, the lid and the container are fitted to obtain leaktight engagement so as to limit the passage of air to the inside of the device in order to limit evaporation during incubation and limit drying out of the hydrating support.

In another variant, the lid and the container are arranged so that in the engaged position, air can flow between the lid and the container so as to obtain controlled ventilation of the hydrating support and thus enhance microbial growth.

According to a characteristic of the invention, the device includes a centering system for relative centering between the lid and the container in order to position each hydrating support in a position that is superposed relative to one or more wells for receiving a respective liquid sample. Such a system facilitates the hydrating operation that consists in bringing the lid and the container close to each other so that each hydrating support comes into contact with a liquid sample and so that this happens simultaneously for all of the hydrating supports.

In an advantageous embodiment variant, the centering system enables the lid to be mounted on the container without there being an assembly direction, such that the relative positioning between the wells and the hydrating supports is symmetrical. Naturally, the lid and/or the container could be provided with keying means so that the lid can be assembled on the container in one direction only.

Advantageously, the device of the invention includes a locking system for locking the lid and the container in a stable position corresponding to the hydrating position. This locking system also makes it possible to reopen the device in order to take material for some other analysis. The locking system may also be designed to provide permanent assembly that is not easy to reopen. In another variant embodiment, the locking system may provide locking that differs depending on the direction in which the lid is mounted on the container, i.e. easily openable in one assembly direction and difficult to open in the other assembly direction. Furthermore, the lid may have keying means so as to ensure only one locking direction.

According to a preferred embodiment characteristic, the container and/or the lid are made of a material that is transparent or translucent. Such a device thus provides the advantage of enabling the reaction obtained by putting the liquid sample into contact with the hydrating support to be read directly, without manipulation.

The hydrating device of the invention presents a particularly advantageous use for detecting and/or identifying and/or enumerating at least one microorganism in a liquid sample that might contain it.

A preferred use of the device of the invention is to determine the sensitivity and the resistance of at least one microorganism to at least one antibiotic.

The invention also provides a method of hydrating at least one hydrating support with a liquid sample by using a device in accordance with the invention.

In order to detect and/or identify and/or enumerate at least one target microorganism in a liquid sample that might contain it, the method comprises the following steps:
- distributing at least one liquid sample in one or more wells of the container;
- positioning the lid and the container in their hydrating position in which each hydrating support is in contact with a liquid sample;
- maintaining the lid and the container in the hydrating position in order to perform an incubation step; and
- reading each hydrating support in order to detect and/or identify and/or enumerate said at least one target microorganism.

The method of the invention thus makes it easy and simple to hydrate a hydrating support with a liquid sample.

The term "detect" is used to mean detecting, with the naked eye or with the help of an optical appliance, the presence of target microorganisms or the existence of growth of target microorganisms.

When the reaction medium from which it is desired to detect the target microorganisms comprises a chromogenic or a fluorogenic substrate, detection may be performed using an optical appliance for fluorogenic substrates, or with the naked eye, or with an optical appliance for chromogenic substrates.

The term "enumerate" specifies counting and/or quantifying the number of target microorganisms, e.g. the number of colonies of bacteria when the target microorganism is a bacterium.

The term "incubate" relates to raising to an appropriate temperature, generally lying in the range 20° C. to 50° C., preferably in the range 30° C. to 45° C., and maintaining that temperature for a time in the range 1 hour (h) to 48 h, preferably in the range 4 h to 24 h.

In an implementation, the method consists in distributing each liquid sample by pouring the liquid sample(s) into the container and by agitating the container in order to ensure that each liquid sample completely fills the reception well(s).

Advantageously, the method of the invention consists in performing the step of reading each hydrating support through the container and/or the lid. It should be observed that, after the incubation step, the method also makes it possible to replace the container with a plane bottom that is transparent or translucent and through which the operation of reading each hydrating support is performed.

Various other characteristics appear from the following description given with reference to the accompanying drawings, which show embodiments of the subject matter of the invention as non-limiting examples.

FIG. 1 is a plan view of a hydrating device in accordance with the invention for hydrating a hydrating support with a liquid sample.

FIG. 2 is a side view of the hydrating device shown in FIG. 1.

Figure 3:
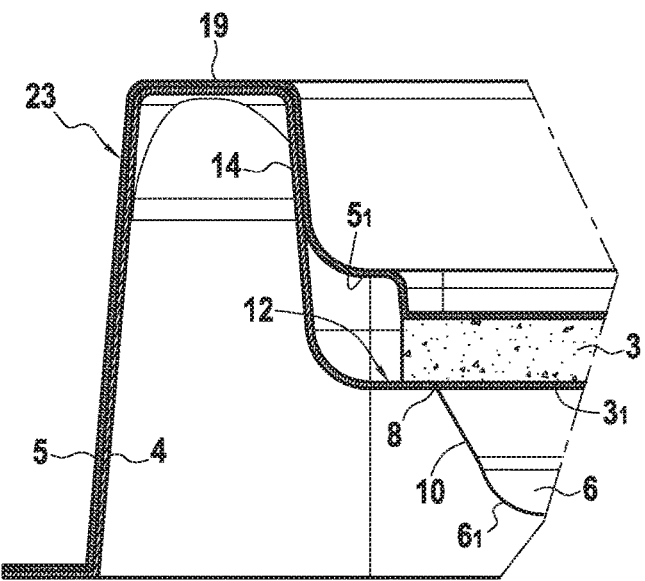
FIG. 3 is a fragmentary elevation section view of the hydrating device shown in FIG. 2.
Figure 4:
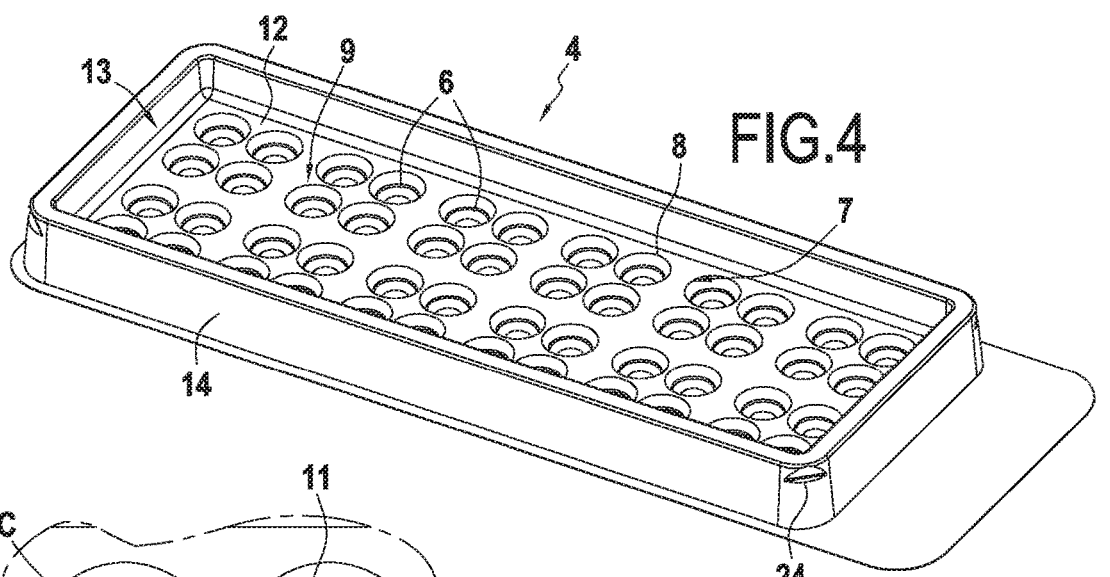
FIG. 4 is a perspective view of an embodiment of a container shown in FIG. 1 and forming part of the hydrating device in accordance with the invention.
Figure 5:
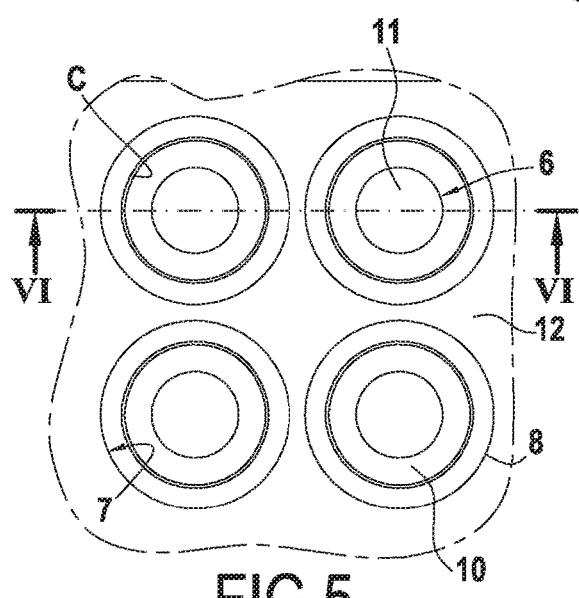
FIG. 5 is a plan view of a detail of the container shown in FIG. 4.
Figure 6:
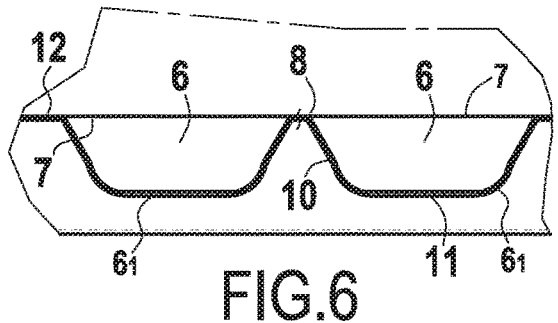
FIG. 6 is a section view on lines VI-VI of FIG. 5, showing the shape of the wells in detail.

As can be seen more clearly in FIGS. 1 to 6, the subject matter of the invention relates to a device 1 for hydrating a hydrating support 3 with a liquid sample 2, the hydrating support including a reaction medium adapted to the liquid sample 2. The device 1 of the invention thus comprises a reception container 4 for receiving at least one liquid sample 2 and a lid 5 fitted with at least one hydrating support 3. As is described in detail in the description below, the device 1 is for occupying a plurality of positions, namely a position waiting to hydrate in which the container 4 does not yet contain the liquid sample 2, and a hydrating position for hydrating the hydrating support(s) 3.

In the hydrating position, after the liquid sample(s) 2 has/have been poured into the container 4, the lid 5 is placed in a superposed position over the container 4 so as to put each hydrating support 3 into contact with a liquid sample 2. The contact zone between the hydrating support 3 and the liquid sample 2 is referred to as the "hydrating interface" in the description below. In an advantageous embodiment, the container 4 and the lid 5 are held in the closed position so that the device 1 occupies an incubation position after which it is possible to perform an operation of reading each hydrating support. The device 1 of the invention comprising the container 4 and the lid 5 is thus in the form of a kit that can easily be used for hydrating a hydrating support 3. In the examples shown in the drawings, the device 1 is rectangular in shape having two opposite sides of small dimensions and two other opposite sides of larger dimensions. The device 1 of the invention finds uses in numerous fields of application.

By way of example, the device 1 of the invention may be used to enable a hydrating support to be hydrated that needs to be rehydrated immediately before use in order to activate the reaction medium of the hydrating support in order to cause the hydrating support that has previously been impregnated with the reaction medium to be made ready for use.

The device 1 of the invention also makes it possible to hydrate a hydrating support impregnated with a reaction medium in order to be able, after incubation, to perform microbiological assay.

Naturally, the reaction medium is selected as a function of the application and of the liquid sample used and of the analyte and/or the microorganisms to be detected or identified and/or enumerated.

In the present invention, the biological sample may be of various origins, e.g. the following origins: food: environmental (water); veterinary; clinical; cosmetic; or pharmaceutical.

Biological samples of clinical origin may correspond to samples taken of biological fluids (total blood, serum, plasma, urine, cephalo-spinal fluid, etc.), stools, samples from the nose, the throat, the skin, wounds, organs, tissues, or isolated cells. This list is naturally not exhaustive.

In general manner, the term "sample" refers to a portion or a quantity (more particularly a small portion or a small quantity) taken from one or more entities for analysis purposes. The sample may optionally be subjected to prior treatment, e.g. involving steps of mixing, diluting, or indeed grinding, in particular if the starting entity is in the solid state.

The biological sample that is taken is generally liable to contain at least one target microorganism, or is suspected of containing one. In most cases, the microorganism is a pathogenic microorganism (such as *Salmonella* or *Vibrio cholerae*) that needs to be detected for public health purposes. The target microorganism may equally well consist in a bacterium that is resistant to antibiotics (antibiotic resistance).

By its nature and its applications, the present invention is particularly adapted to analyzing biological samples of potentially moderate to large pathogenic power (possibly even extremely large), such as a sample of cholera diarrhea.

In the meaning of the present invention, the term "microorganism" covers Gram positive or Gram negative bacteria, yeasts, molds, amoebas, and more generally single-cell organisms that are invisible to the naked eye, and that can be manipulated and caused to multiply in a laboratory.

In a preferred embodiment of the invention, the microorganism is a Gram negative or Gram positive bacterium.

As Gram positive bacteria, mention may be made of bacteria of the following genera: *Enterococcus, Streptoccus, Lactobacillus, Bifidobacterium, Staphylococcus, Bacillus, Listeria, Clostridium, Mycobacteria, Nocardia, Corynebacteria, Micrococcus*, and *Deinococcus*.

As Gram negative bacteria, mention may be made of bacteria of the following genera: *Salmonella, Eschericia coli, Pseudomonas*, and *Vibrio cholerae*.

As yeasts, mention may be made of bacteria of the following genera: *Candida, Cryptococcus, Saccharomyces*, and *Trichosporon*.

As molds, mention may be made of bacteria of the following genera: *Asperigillus, Penicillium*, and *Cladosporium*.

Selecting and pretreating liquid samples of biological, industrial, or environmental nature are operations that are well known in the state of the art and they are not described in greater detail. Likewise, the reaction medium impregnating the hydrating support 3 may be of any appropriate nature depending on the intended application. For example, the reaction medium may be a chromogenic culture medium enabling the looked-for microbe species to have a specific color, or merely a medium for developing analytes of interest without any provision of nutrients since the nutrients required for microbial physiology are provided by the liquid for analysis (as for milk).

The term "reaction medium" is used to mean a medium including all of the elements necessary for the survival and/or growth of microorganisms. The reaction medium may serve solely as a developing medium, or else as a culture and developing medium. In the first situation, the microorganisms are cultured beforehand, whereas in the second the reaction medium also constitutes the culture medium.

The term "developing medium" is used to mean any medium containing a molecule capable of coupling with the microorganisms or the bonding partners of said microorganisms and making it possible by their transduction properties (fluorescence, staining, radioactivity, etc.) to reveal the presence of said microorganisms. The presence of target microorganisms may be developed so as to be visible (to the naked eye) or by optically reading a stain or fluorescence on all or part of the support.

The term "culture medium" is used to mean a medium including all of the elements necessary for the survival and/or growth of microorganisms. In practice, the person skilled in the art selects the culture medium as a function of the target microorganisms, using criteria that are well known and within the competence of such a person skilled in the art.

The reaction medium of the invention may contain optional additives such as, for example: peptones, one or more growth factors, carbohydrates, one or more selective agents, buffers, stains, one or more gelifiers, hydrogels, viscosity agent, etc.

Such a reaction medium impregnates the hydrating support 3 in any appropriate manner known to the person skilled in the art. Thus, the hydrating support may be put into solution in water or in a solvent and then dried. The hydrating support may also be impregnated by a dehydrated reaction medium, as described in international patent application PCT/FR2015/050035 filed by the Applicant. The hydrating support 3 is made of any material that is suitable for integrating and conserving the reaction medium within itself, so that it can subsequently be hydrated by a liquid sample. For this purpose, the hydrating support 3 is made on the basis of various absorbent compounds having very great power for retaining water such as viscose, rayon, cotton, natural or chemically-modified cellulose fibers such as carboxymethyl cellulose, absorbent or superabsorbent chemical polymers such as salts of polyacrylate, or acrylate/acrylamide copolymer. The hydrating support has a volume of appropriate porosity in the form of woven or non-woven fabric presenting an array of fibers or filaments, or a foam with open pores.

The container 4 of the device of the invention is adapted to receive one or more liquid samples 2, depending on the number of hydrating supports 3 that are to be hydrated. In the examples shown in the drawings, the container 4 is adapted to receive a plurality of liquid samples 2, each of which is to be put into contact with a respective hydrating support 3. In the examples shown in the various figures, the lid 5 is provided with twelve hydrating supports 3, such that the container 4 is for receiving twelve liquid samples 2. Naturally, the lid 5 may have some other number of hydrating supports 3. Likewise, the container 4 may receive some other number of liquid samples.

Each liquid sample 2 is to be contained in one or more wells 6 arranged in the container 4. The container 4 is thus configured as a function of the number of wells 6 selected to receive each liquid sample and as a function of the number of liquid samples used, which is generally equal to the number of hydrating supports 3, even if it is possible to envisage not hydrating one or more of the hydrating supports 3 of the container 4. The well(s) 6 for receiving a liquid sample 2 is/are thus arranged to be situated facing or in register with the hydrating support 3 that is to be hydrated by said liquid sample.

In position for receiving a liquid sample, the container 4 is positioned in a horizontal plane so that each well 6 is upwardly open in order to recover the liquid. Each well 6 thus has an inlet orifice or opening 7 at a top edge 8 of the well from which at least one cavity $6_1$ extends downwards. By definition, it is considered that each well 6 possesses an inlet orifice 7 of outline C formed by the top edge 8, which is closed, i.e. which forms a loop.

In the example shown, the container 4 comprises a plate 9 in which the well(s) 6 is/are arranged so as to form indentations. Each well 6 thus has at least one cavity $6_1$ presenting a wall 10 extending over a limited height between a closed bottom 11 and a peripheral rim 12 surrounding the top edge 8 of the well. The wall 10 extends below or set back from the peripheral rim 12, which serves as an abutment and a bearing surface for the hydrating support 3 in the hydrating position, as can be understood from the description below. Each well 6 thus possesses a calibrated content or volume that is defined at the level of its top edge 8, which well is empty prior to being filled with the liquid sample. Likewise, each well 6 possesses an area at its orifice 7 that is accurately calibrated.

According to an advantageous embodiment characteristic, the container 4 is arranged to define at least one distribution bowl 13 for distributing the liquid sample(s) in the well(s) 6. For this purpose, the container 4 has a peripheral margin 14 extending upwards from the plate 9 surrounding all of the wells 6 so as to define the bowl 13 therein. As can be seen in the figures, the container 4 thus possesses at its periphery a peripheral margin 14 that extends upwards from the peripheral rims 12 around the various wells, these rims 12 extending in a plane below which the well(s) 6 is/are situated. This peripheral margin 14 enables the liquid sample to be confined without any risk of overflow during the operation of filling the wells.

The liquid samples 2 are distributed within the wells 6 in simple manner since it suffices to pour the total volume corresponding to the liquid samples that are to be distributed in the various wells into the inside of the bowl 13 so that the liquid becomes established in the various wells.

This distribution may optionally be encouraged by a stage of agitating the container 4 so as to ensure that each liquid sample completely fills the reception wells provided. If the sample is transparent, each well 6 could be provided with a stain for the liquid sample in order to assist filling said well.

According to another advantageous embodiment characteristic, at least some of the wells 6 are provided with microchannels 16 for making it easier to feed the liquid sample to the wells.

Figure 15:
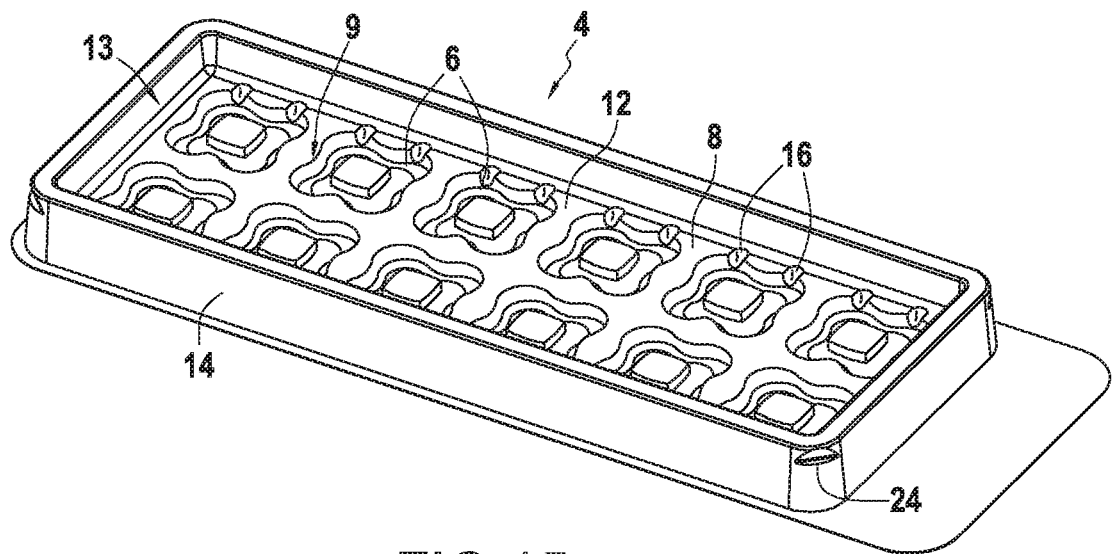
FIG. 15 is a perspective view of another embodiment of a container having wells, each presenting a plurality of cavities with an island arranged in the center.

Advantageously, all of the wells 6 adjacent to the peripheral margin 14 are provided with microchannels 16. Thus, and as can be seen in FIG. 15, each well 6 adjacent to the peripheral margin 14 includes at least one microchannel 16 (two in the example shown) provided in the plate 9 of the container 4 so as to open out at the top edge 8 of the well 6. Each microchannel 16 thus has a top edge 8 in continuity with the top edge 8 proper of said well 6 such that the outline C of the well including the microchannel(s) 16 is closed. It should be considered that the well 6 and the microchannel 16 define a calibrated reception volume for receiving a liquid sample 2 by considering that each microchannel is closed at its end opposite from its end communicating with the well. Likewise, each microchannel 16 presents at its top edge 8 an area that is calibrated accurately.

Advantageously, each microchannel 16 extends from the top edge 8 of the well towards the peripheral margin 14, and preferably up to the peripheral margin 14 so that when the liquid flows along the peripheral margin it is recovered by the microchannels 16 so as to be taken into the wells 6.

Thus, the microchannels 16 are situated at least in part outside the hydrating interface such that in the hydrating position the microchannels 16 project beyond the hydrating support 3. Typically, each microchannel 16 projects at least 1 millimeter (mm) beyond the hydrating support 3. In addition to the fact that the microchannels make it easier to distribute the liquid samples in the wells, the microchannels 16 also serve after the hydrating operation to facilitate exchanging air inside the device 1.

Figure 7:
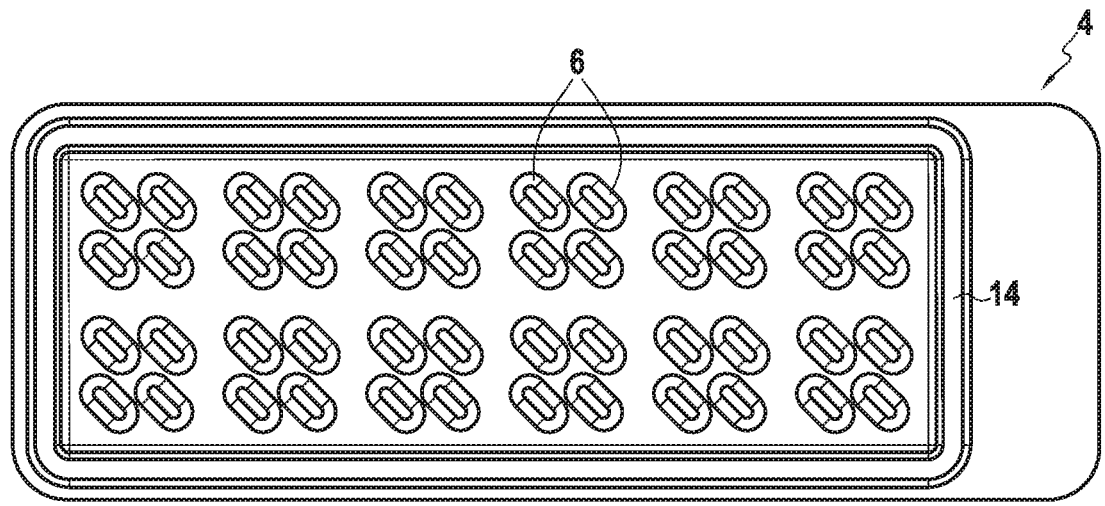
FIG. 7 is a plan view of another embodiment of a container including reception wells of sloping oblong shape.
Figure 8:
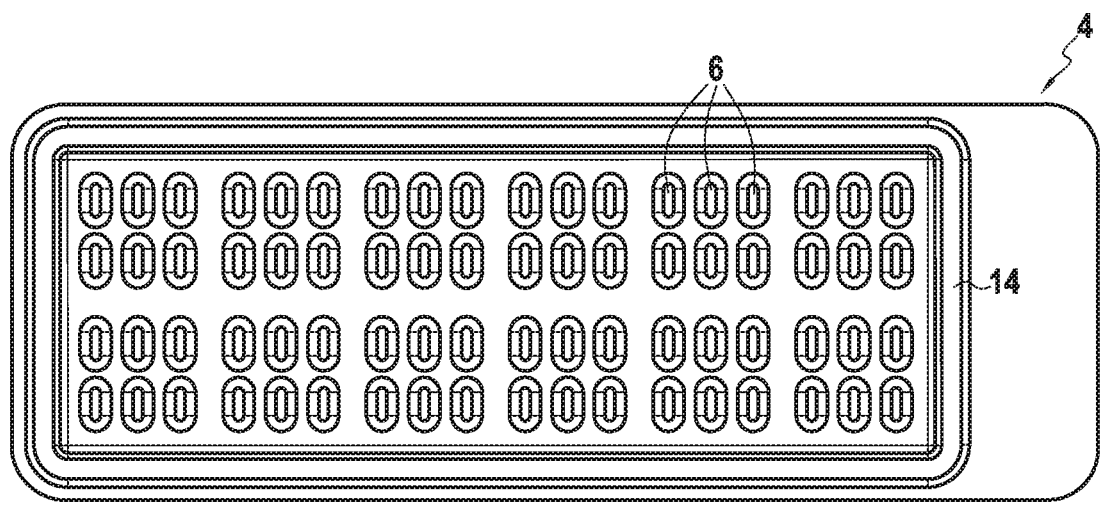
FIG. 8 shows another embodiment of a container having reception wells of oblong shapes that are oriented parallel to a side of the container.
Figure 9:
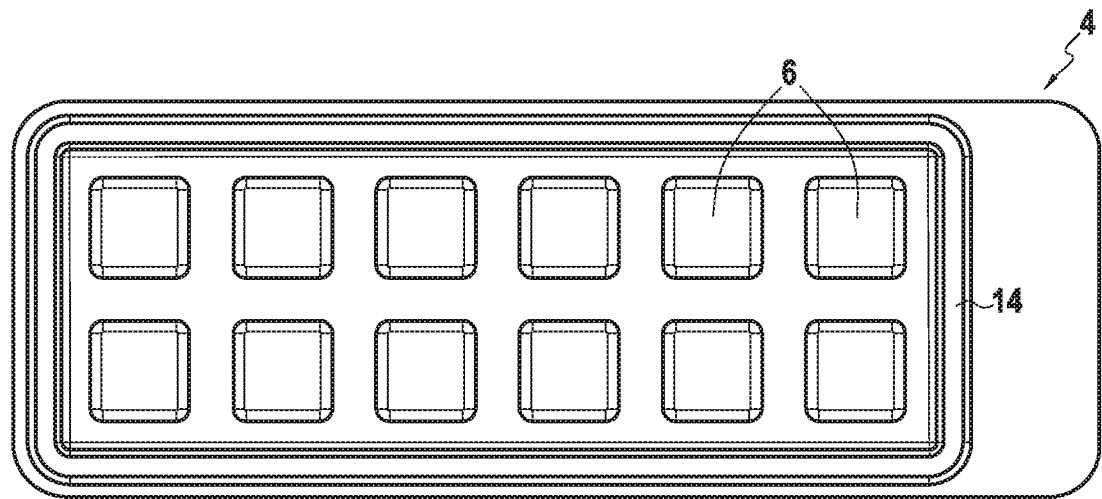
FIG. 9 is a plan view of another embodiment of a container having wells of square shape, each serving to receive a liquid sample.
Figure 10:
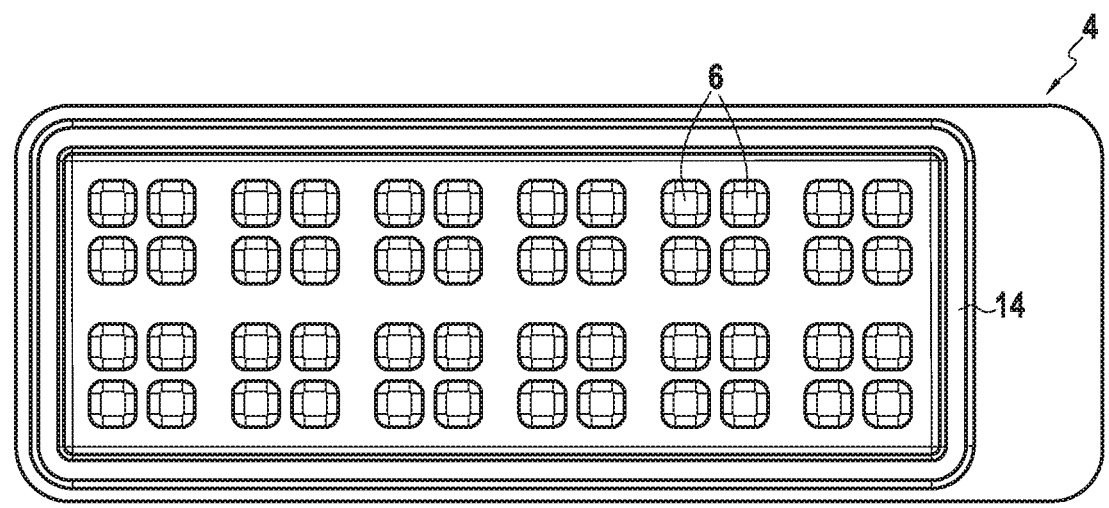
FIG. 10 is a plan view of another embodiment of a container having wells of square shape grouped together in fours so that each group of wells serves to receive a liquid sample.

In the embodiment shown in FIGS. 1, 7, and 10, each liquid sample 2 is distributed in a group of four wells 6 such that the container 4 that can receive twelve liquid samples 2 has forty-eight wells 6. In the embodiments shown respectively in FIGS. 8, 9, and 16, the number of wells 6 forming a liquid sample reception group is respectively six, one, and two. In these embodiments shown in FIGS. 8, 9, and 16, the container 4 may receive twelve liquid samples 2.

Figure 11:
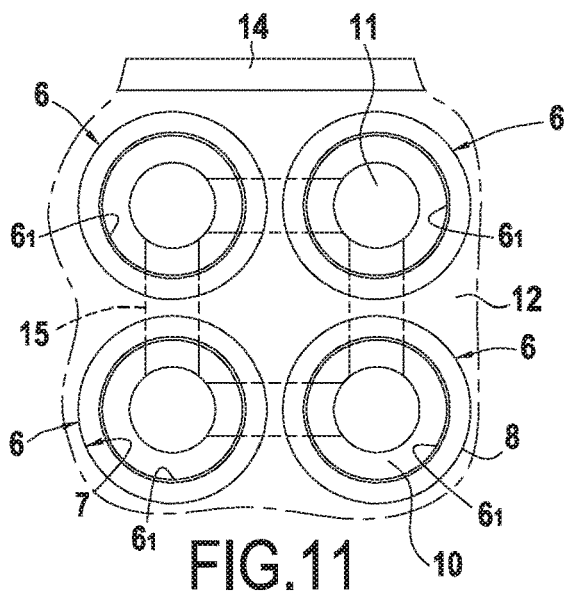
FIG. 11 is a plan view of an embodiment of a reception well having four cavities of circular section that communicate with one another via their bottoms.

Naturally, the number of wells 6 for receiving a liquid sample and subsequently for hydrating a hydrating support 3 may be different from the examples shown. Furthermore, in the examples shown in FIGS. 1, 7, 8, and 10, the wells 6 belonging to the same liquid sample reception group are independent of one another, insofar as none of the wells belonging to a given group communicates with any other well. Nevertheless, provision may be made for the cavities $6_1$ of the liquid sample reception wells 6 to communicate with one another via link ducts 15 while each well 6 conserves a closed outline at its top edge 8. As shown in FIG. 11, the link ducts 15 connect together in pairs the bottoms 11 of the cavities $6_1$ of four wells that are together to receive one liquid sample.

Naturally, the wells 6 may receive different possible shapes adapted to hydrating the hydrating support 3. Thus, and as can be seen in the figures, the wells 6 may present a shape that may for example be hemispherical, oblong, conical, or prismatic.

On the same lines, the inlet opening 7 of each well 6 may present various shapes in order to ensure uniform hydrating of the hydrating support 3. Thus, the inlet opening 7 of each well 6 may present a shape that is round (FIG. 1), oblong (FIGS. 7, 8), or square (FIGS. 9, 10).

By way of example, FIGS. 12 to 16 show various other embodiments for the inlet openings 7 of the wells 6. In these examples, the inlet openings 7 of each well 6 possesses a closed outline C having various lobes of various profiles arranged in a circular arc or in other ways. In the examples shown in FIGS. 12 and 13, each well 6 has four cavities $6_1$ arranged at the four corners of a square, being spaced apart a little from one another. These four cavities $6_1$ are connected together via the center of the square in such a manner that the well 6 possesses a single inlet orifice 7 defined by a continuous top edge 8 that forms a closed loop. The orifice 7 of the well 6 thus presents a shamrock shape.

Figure 12:
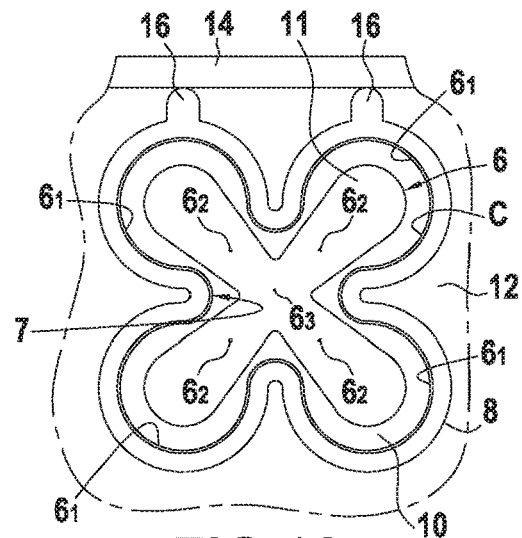
FIG. 12 is a plan view of an embodiment of a reception well having four cavities of circular section communicating with one another via their top edges.

In the embodiment shown in FIG. 12, each of the four cavities $6_1$ possesses a section in the form of ¾ of a circle and the cavities communicate with one another via communication passages $6_2$ leading into a central zone $6_3$ of the orifice 7. For example, each communication passage $6_2$ possesses a width that is greater than the radius of the circle defining the cavity but less than the diameter of said circle.

Figure 13:
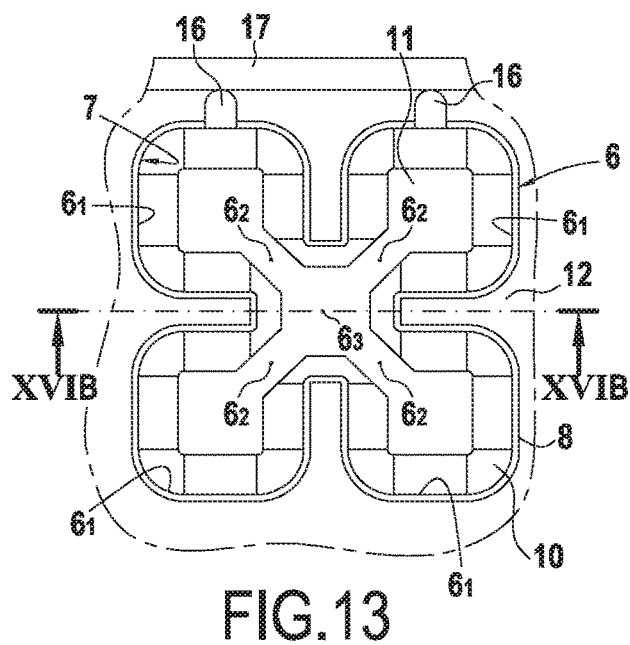
FIG. 13 is a plan view of another embodiment of a reception well having four cavities of square section that communicate with one another in a central zone via their top edges.

In the example shown in FIG. 13, each of the four cavities $6_1$ possesses a square section and the cavities communicate with one another via communication passages $6_2$ arranged in the neighboring corners of said cavities so as to open out into a central zone $6_3$ of the orifice 7 that presents an area of the same order as the area defined by the square section of one of the cavities $6_1$.

Figure 14:
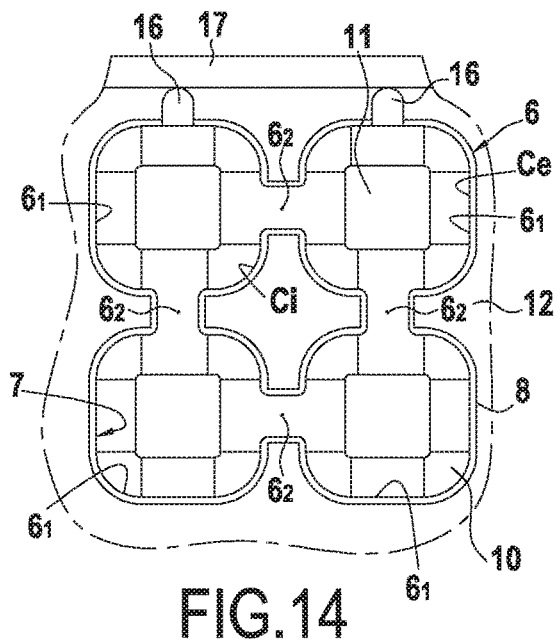
FIG. 14 is a plan view of another embodiment of a reception well having four cavities of square section that communicate with one another in pairs via their top edges.

In the embodiment shown in FIG. 14, the four cavities $6_1$ are likewise square in section and arranged at the four corners of a square, but the cavities $6_1$ communicate with one another in pairs via communication passages $6_2$. Thus, the orifice 7 presents a closed outer outline $C_e$ and a closed inner outline $C_i$ forming an island in the center of the orifice 7. Naturally, the open hydrating section of the well 6 is situated between the outer and inner outlines $C_e$ and $C_i$.

Figure 15A:
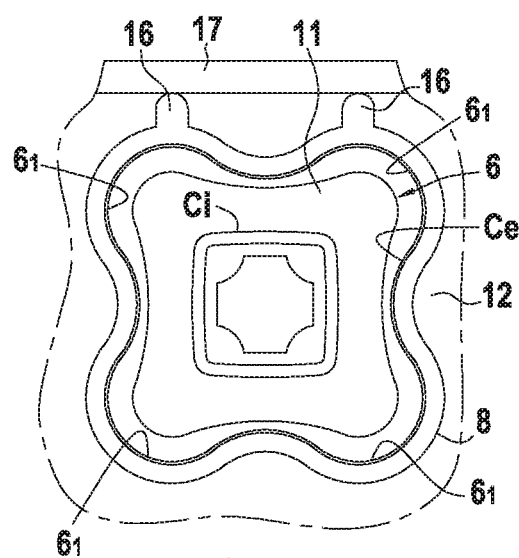
FIG. 15A is a plan view of a well arranged in the container shown in FIG. 15.

FIGS. 15 and 15A show another embodiment that is substantially analogous to the embodiment shown in FIG. 14 except that the cavities $6_1$ are circular in section and they are connected together by curved profiles. In this example, the orifice 7 of each of the wells 6 presents an outer closed outline $C_e$ and an inner closed outline $C_i$ forming an island in the center of the orifice 7. In the embodiment described with reference to FIGS. 12 to 15, each well 6 has four cavities $6_1$ that are interconnected. Naturally, the number of cavities forming a well may be other than four.

Figure 16:
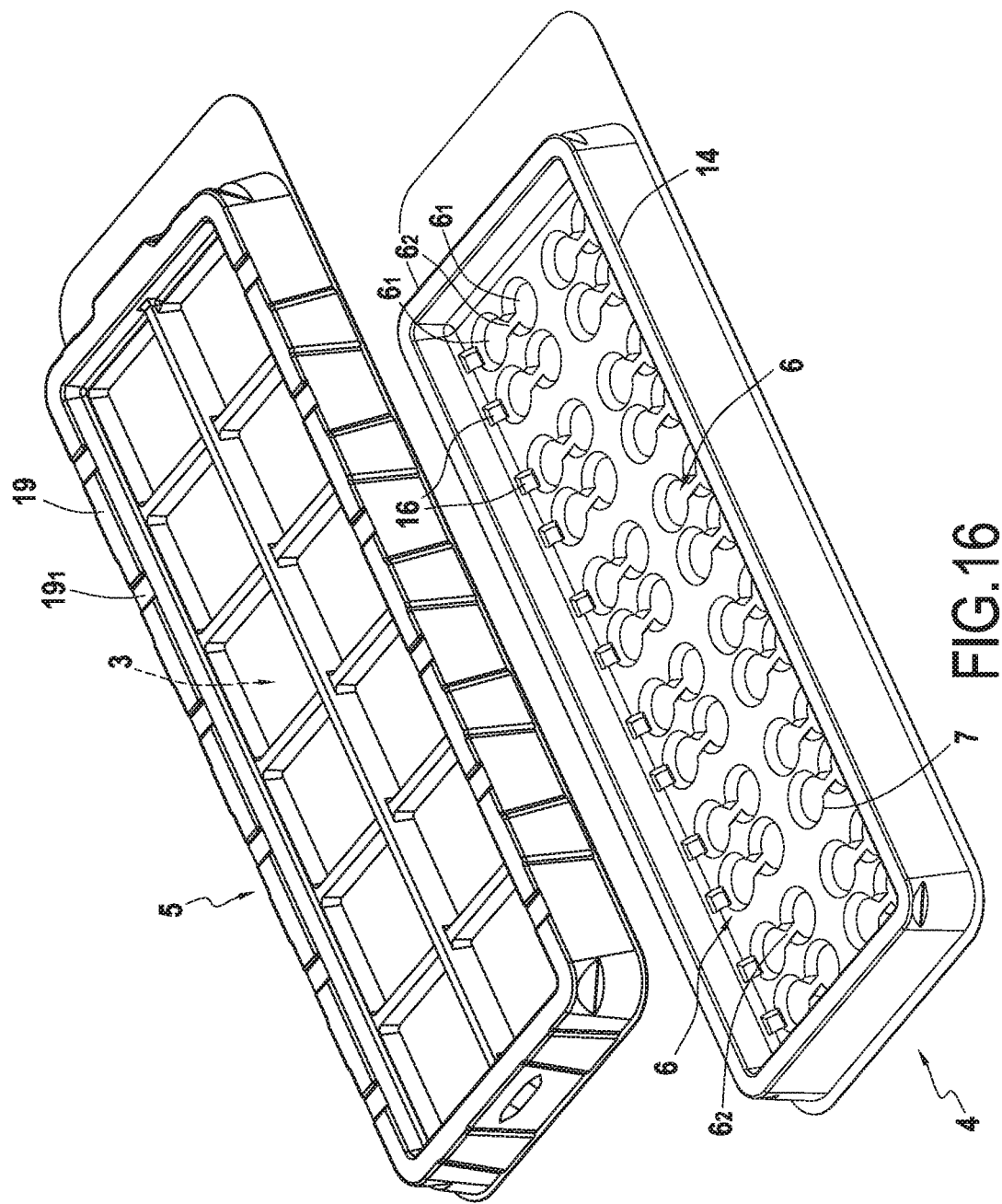
FIG. 16 is a perspective view of another embodiment of a hydrating device in accordance with the invention in which the container has reception wells, each having two cavities that are connected together.

FIG. 16 shows another embodiment that is substantially analogous to the embodiment shown in FIG. 12 except that the four liquid sample reception cavities $6_1$ are arranged in pairs. Each well 6 comprises two cavities $6_1$ that are connected together. The two cavities $6_1$ of a pair communicate with each other via a communication passage $6_2$. Thus, the orifice 7 of a well 6 presents a generally oblong shape since, at each end, it presents a section in the form of ¾ of a circle, while in its central portion it presents a communication passage $6_2$ of rectilinear section of width that is less than the diameter of the section in the shape of ¾ of a circle.

Advantageously, this communication passage $6_2$ is centered relative to the sections in the shape of ¾ of a circle.

It should be observed that in this variant embodiment, all of the wells 6 are provided with microchannels 16. More precisely, the cavity $6_1$ of each well that is closer to the peripheral margin 14 is provided with a microchannel 16 extending towards the peripheral margin 14.

Advantageously, the orifice 7 of a well 6 is arranged so that the oblong shape is oriented parallel to the side of the container presenting the smaller size. Rocking the container during the operation of distributing the liquid sample in the wells relative to the longer side of the container thus enables the liquid to be well distributed in the well.

According to an advantageous embodiment characteristic, at least one well 6 presents a profile that narrows going away from its edge 8. Thus, and as can be seen more precisely in FIGS. 3 and 6, the wall 10 of the well 6 extends from the rim 12 at an obtuse angle such that the well presents a shape that flares going towards its top edge 8. The profile of the well 6 that narrows going towards its bottom may be restricted to a fraction of the height of the wall 10 or it may be continuous between the top edge and the bottom of the well. In another embodiment variant, provision may be made for the wall 10 to extend substantially at right angles relative to the peripheral rim 12, optionally being provided with a flared shape at the level of its top edge 8.

As explained above, each liquid sample 2 is received via one or more reception wells 6. In the example shown in FIGS. 1, 7, 10, and 11, each liquid sample 2 is received by four wells 6, whereas in the example shown in FIG. 16, each liquid sample 2 is received by two wells 6. In other words, the total volume of a liquid sample 2 is distributed in these examples either in the four allocated wells 6, or else in two wells 6, and indeed also in the microchannels 16 that feed them. Each liquid sample 2 is to be absorbed by a hydrating support 3 when the lid 5 and the container 4 are placed in the hydrating position.

For this purpose, the lid 5 possesses a bottom face 5$_1$ on which at least one hydrating support 3 is fastened so as to present an absorption face 3$_1$ for a liquid sample 2. This absorption face 3$_1$ is for positioning over the container 4 so as to come into contact with the liquid sample 2 via the hydrating interface. The hydrating supports 3 are fastened on the lid 5 using any known fastening system. For example, each hydrating support 3 may be fastened using a heat-sealing method or using a film of adhesive or glue interposed between the lid 5 and the hydrating support 3 opposite from its absorption face 3$_1$. In order to facilitate assembly, the bottom face 5$_1$ of the lid may present housings in which the hydrating supports 3 are received in part.

In accordance with a characteristic of the invention, each hydrating support 3 presents an absorption face 3$_1$ of area that is greater than the area of the calibrated open section of the container 4 that enables the hydrating support to be hydrated by a liquid sample 2. This hydrating calibrated section presented by the container 4 corresponds to the liquid surface of each sample, that is to come into contact with the hydrating support in the hydrating position and that is situated level with the top edge 8 of the well(s) 6 and optionally also of the microchannels 16. It should be observed that this hydrating calibrated section does not necessarily correspond to the calibrated open section of the wells 6 and of the microchannels 16 insofar as this entire section is not necessarily in contact with the absorption face 3$_1$ of the hydrating support 3, as explained in the description below.

When a liquid sample 2 is received in a single well 6, the hydrating area of the calibrated open section of the container for a liquid sample corresponds to the area of the calibrated open section of the well 6, this open section being defined by the orifice 7 of the well 6. It should be observed that the well 6 may have one or more cavities 6$_1$.

When a liquid sample 2 is shared among a plurality of wells 6, the hydrating area of the calibrated open section for receiving a liquid sample corresponds to the sum of the calibrated open sections of the various wells 6, these open sections being defined by the orifices 7 of the various wells 6. It should be observed that these wells 6 may each have one or more cavities 6$_1$ that are independent or else connected to one another via their bottoms.

When a well 6 is provided with at least one feed microchannel 16, the well 6 and the microchannel 16 together define a calibrated reception volume for a liquid sample resulting from the sum of the volumes of the well and of the microchannel. The well 6 and the microchannel 16 present a hydrating calibrated open section defined by the top edge 8 of the well 6 and by the top edge 8 of at least a portion of the microchannel 16 that is to be in contact with the absorption face 3$_1$ of the support. Naturally, a portion of the microchannel 16 situated outside the absorption face 3$_1$ of the hydrating support does not form part of this hydrating calibrated open section.

In an embodiment characteristic, the area of the calibrated open section enabling a hydrating support 3 to be hydrated by a liquid sample is such that the ratio of this calibrated open section for hydrating a hydrating support with a liquid sample over the area of the absorption face 3$_1$ of the hydrating support 3 lies in the range 40% to 80%, preferably in the range 50% to 75%, and more advantageously in the range 55% to 65%. In other words, the surface of the absorption face 3$_1$ of the hydrating support 3 is designed to come into direct contact with the liquid sample over substantially ⅔ of its area. For example, the absorption face 3$_1$ of each hydrating support 3 possesses an area of 400 square millimeters (mm$^2$), and the areas of the hydrating open sections defined by the wells 6 of outlines corresponding respectively to the profiles of the embodiments shown in FIGS. 12, 13, 14, and 15 are respectively 278 mm$^2$, 260 mm$^2$, 266 mm$^2$, and 270 mm$^2$. Likewise, the area of the hydrating open section defined by the two wells 6 of the embodiment shown in FIG. 16 is 222 mm$^2$ with the absorption face 3$_1$ having an area of 400 mm$^2$. Thus, the ratio of the hydrating area presented by a well on the absorption surface 3$_1$ is respectively 70%, 65%, 67%, 68%, and 55% in the examples shown in FIGS. 12, 13, 14, 15, and 16.

It should be observed that the shape and the dimensions of the open section of the well 6 defined by the orifices 7 and also the positioning of the orifices 7 relative to the hydrating supports 3 are selected to optimize hydrating the hydrating support 3 in particular in such a manner as to avoid causing a liquid migration front to appear inside the hydrating support 3. Thus, the orifices 7 possess a shape that is circular, oblong, or square in the examples shown respectively in FIGS. 1, 7, and 10. Furthermore, in the example shown in FIG. 8, the orifices 7 of oblong shape are arranged so as to be oriented parallel to one edge of the hydrating support, whereas in the example shown in FIG. 7, the orifices 7 of oblong shapes are arranged so as to be oriented obliquely relative to an edge of the hydrating support.

In the embodiments shown in FIGS. 12 to 16, the orifices 7 of the wells 6 are arranged with a shape limiting transverse migration of the liquid inside the hydrating support. For this purpose, each well 6 presents a hydrating calibrated open section defined by an outline C, Ce, Ci of shape that is selected so that none of the points lying between the outside of said section and the outline of said absorption face 3$_1$ is situated at a linear distance of more than 3 mm from the outlines nearest to said face or said section. In other words, the shape of the orifice 7 is selected so as to spread the hydrating interface as uniformly as possible over the absorption face 3$_1$ of the hydrating support. Thus, the distance to be traveled by the liquid in order to hydrate all of the hydrating support is limited to a maximum value in order to avoid creating a liquid migration front. Furthermore, the distance to be traveled by the liquid is substantially identical at all points from the outline C of the well. It should be understood that each hydrating support 3 presents a surface area that enables its absorption face 3$_1$ to cover a hydrating calibrated open section of the container completely. Thus, for example, when the liquid sample 2 is shared among four wells 6, each hydrating support 3 in the hydrating position has its absorption face 3$_1$ completely covering the four orifices 7 of the four wells.

Advantageously, each hydrating support 3 completely covers a calibrated open section for receiving a liquid sample 2 while leaving a peripheral belt 17 that remains on its absorption face 3$_1$ between said section and the peripheral edge 3$_2$ of the hydrating support, which belt, in the hydrating position and away from the microchannels 16, is not in contact with the open section of the well(s). Thus, each hydrating support 3 in the hydrating position is positioned so that the orifice 7 of the well(s) 6 is positioned outside this peripheral belt 17, i.e. is set back from the peripheral edge 3$_2$, so that the liquid of the wells and of the microchannels is absorbed completely by the hydrating support without any risk of leakage via the edges of the hydrating support.

It can be seen from the above description that the profile or the shape of the hydrating calibrated open section defined by the wells (and possibly also the microchannels) is selected so as to avoid forming a liquid migration front in the hydrating support. Furthermore, the shape and/or the dimensions of the wells 6 are selected so as to enable the liquid sample received by such wells to be accurately calibrated. Advantageously, each well 6 has a plurality of cavities $6_1$ for receiving a portion of the liquid sample, these reception cavities communicating with one another at least via the hydrating calibrated open section of outline C that possesses various lobes. Thus, well 6 presents a hydrating calibrated open section defined by an outline of shape that is selected so that none of the points taken inside said section is situated at a linear distance of more than 4 mm from the closest outline of said section. Such a characteristic avoids any need to make reception cavities of dimensions that are too great, which would not enable the sample to be measured accurately.

In complementary manner, each well 6 presents a hydrating calibrated open section defined by an outline C of shape that is selected so that the smallest dimension of the section is greater than 1.5 mm. In other words, such a characteristic avoids making reception cavities $6_1$ with dimensions that are too small, which would lead to difficulty in filling the wells with the sample.

According to an advantageous characteristic, it should be considered that the reception wells 6, optionally including the feed microchannels 16, define a calibrated volume such that in the hydrating position each liquid sample 2 is completely absorbed by the hydrating support 3. Thus, depending on the number of wells 6 receiving a liquid sample, the wells are dimensioned in volume so as to ensure complete absorption of the liquid sample by the hydrating support 3. For this purpose, each well 6 possesses a depth that is limited, typically in the range 1 mm to 5 mm, more preferably in the range 2 mm to 3 mm. Furthermore, according to an advantageous characteristic, the calibrated volume of the reception wells 6, optionally including the microchannels 16, is determined so that each hydrating support 3 is completely hydrated by a liquid sample 2.

According to an advantageous embodiment characteristic of the invention, the hydrating supports 3 are spaced apart from one another by separation corridors 18 so as to separate the hydrating supports from one another and consequently separate the liquid samples. Such an arrangement thus prevents cross-contamination between the hydrating supports 3.

Typically, the hydrating supports 3 are separated from one another by a distance of about 3 mm. Furthermore, arranging corridors 18 between the hydrating supports 3 allows air to circulate between the hydrating supports 3 and provides for good aeration in particular during the incubation stage, as explained in the description below.

In a preferred embodiment, when the lid 5 has a plurality of hydrating supports 3, each of which is to be hydrated by a liquid sample, the number and the volume of the wells 6 facing each hydrating support are identical for all of the hydrating supports. Such an arrangement makes it possible to perform comparison concerning the reaction of the reaction medium. Naturally, some other arrangement could be envisaged in which the number and the volume of the wells 6 facing each hydrating support are different for the various hydrating supports.

Naturally, the container 4 may include at least one separation partition in order to define at least two bowls 13 for distributing different liquid samples from one bowl to the other. This separation partition is arranged to connect together two zones of the peripheral margin 14 that are situated on two opposite or adjacent sides of the container. The bowls 13 may thus receive liquid samples that differ in terms of composition and/or dilution. Likewise, a bowl 13 may be designed to receive a liquid sample having the purpose of hydrating a hydrating support in order to maintain a determined degree of humidity inside the device 1.

In the above-described variant embodiments, each bowl 13 is arranged to confine the liquid sample(s) insofar as the plate 9 and the peripheral margin 14 do not include holes. In another variant embodiment, it should be observed that the bowl 13 could include at least one outlet orifice to enable excess poured liquid sample to be removed. Under such circumstances, a liquid sample is poured in having a volume that is greater than the total volume of the wells, and the excess sample is emptied out via a pierced well positioned outside the hydrating supports. Such an embodiment variant finds an advantageous application by way of example with a hydrating support for detecting cholera.

According to an advantageous embodiment characteristic of the device 1 of the invention, the lid 5 possesses a peripheral groove 19 suitable for engaging on the peripheral margin 17 of the container in the hydrating position.

Advantageously, the device 1 of the invention includes a system 23 for relative centering between the lid 5 and the container 4 in order to position each hydrating support 3 in a position where it is superposed over one or more liquid sample reception wells. In a preferred embodiment characteristic, the centering system is provided by the peripheral groove 19 engaging on the peripheral margin 14 of the container. Thus, assembling the lid 5 and the container 4 together makes it possible to obtain accurate positioning of the hydrating supports 3 such that each of them completely covers the orifice of the well(s) containing a liquid sample.

In a variant embodiment, the peripheral groove 19 and the peripheral margin 14 are adjusted so as to obtain leaktight engagement.

In another embodiment variant, the peripheral groove 19 and the peripheral margin 14 are arranged so as to allow air to flow between the lid and the container so as to obtain controlled ventilation of the hydrating supports. For example, and as can be seen in FIG. 16, the peripheral groove 19 is provided locally with abutments $19_1$ coming to bear against the peripheral margin 14 of the container, so as to allow air to flow between the abutments.

It should be understood that engaging the lid 5 on the container 4 by co-operation between the peripheral groove 19 and the peripheral margin 14 provides guidance during relative approach suitable for bringing each hydrating support 3 into contact with the liquid sample. For this purpose, each hydrating support 3 is designed to come into contact with or in abutment against the peripheral rims 12 of the wells so that the absorption face $3_1$ of each hydrating support is positioned at the top edges 8 of a well. In this "hydrating" position, the liquid sample is absorbed by capillarity by the hydrating support placed facing it.

It should be observed that the device 1 of the invention may include a locking system 24 for locking the lid 5 and the container 4 together in a stable position corresponding to the hydrating position so as to keep the lid and the container in a closed position. Such a locking system 24 may be provided, for example, by means of a lug formed on the peripheral margin 14 of the container for the purpose of blocking the lid 5 on the container 4 when in the closed position.

According to an advantageous embodiment characteristic, the container 4 and/or the lid 5 are made of a material that is transparent or translucent in order to enable the hydration or the activation that is performed to be read directly. For example, the container 4 and the lid 5 may be made of polyethylene terephthalate (PET) or in another example using polyvinylchloride (PVC) or indeed polypropylene (PP) or polylactic bioplastic (PLA) of renewable and biodegradable vegetable origin, by conventional thermoforming or injection-molding techniques. Additionally, the container 4 and/or the lid 5 may incorporate optical systems for improving the visual quality of the hydrating supports 3. Furthermore, the container 4 and the lid 5 are of complementary shapes, specifically of rectangular shape in the example shown, however it is clear that the container and the lid could be of some other shape. Finally, the container 4 and the lid 5 may be hinged together about hinges or they may be presented in the form of two independent parts.

The device 1 of the invention enables a method of hydrating supports with liquid samples to be performed in simple manner.

Figure 17A:
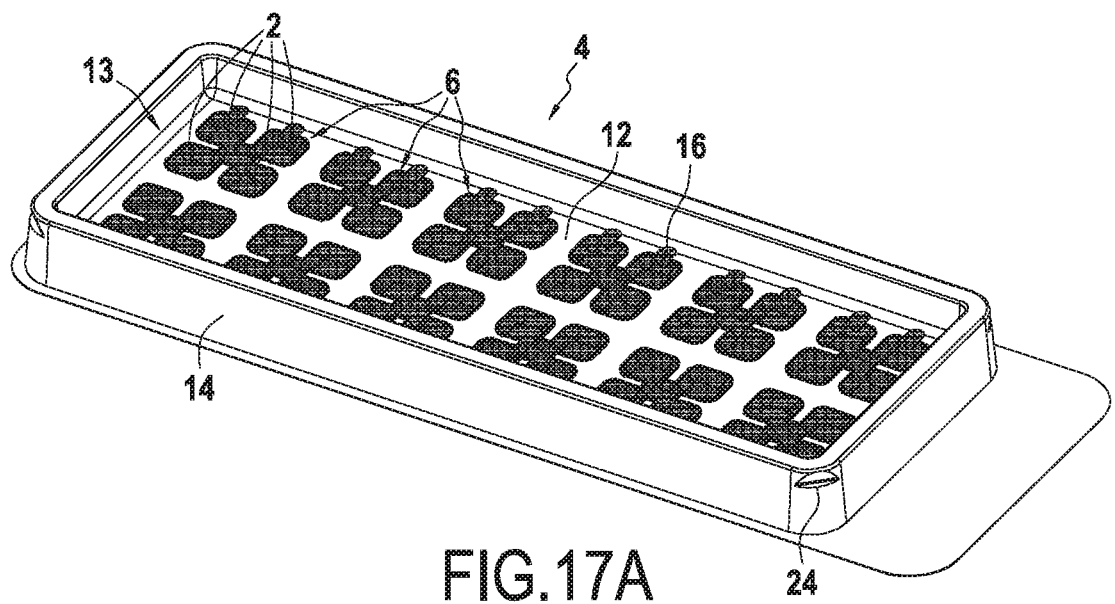
FIG. 17A is a perspective view showing a container in which the wells are filled with liquid samples.

The first step consists in completely distributing each liquid sample in one or more wells 6 of the container 4. In the example shown in FIG. 17A, each sample is for distributing in a well 6 comprising four cavities that are interconnected in the manner shown in FIG. 13. Naturally, when the lid 5 is positioned on the container, the lid 5 is removed in order to enable the sample volume to be poured into the inside of the liquid distribution bowl 13. In an example under consideration, each liquid sample 2 presents a volume of 500 microliters (μL) that is to be distributed in the four interconnected cavities of the wells 6. The lid 5 possesses twelve hydrating supports 3 such that the container 4 is to receive twelve liquid sample volumes, i.e. a total volume of 6 milliliters (mL). A liquid volume of 6 mL is thus poured into the bowl 13 of the container 3. This distribution is defined by the volume presented by the wells 6.

The distribution of each liquid sample is performed by tilting and/or agitating the container 4 a little so as to be able to distribute the liquid in the various wells. This agitation is performed manually or alternatively by using an automatic mechanism. Such agitation is stopped when all of the wells 6 have been filled by the liquid sample, i.e. when the level of the liquid reaches the top edges 8 of the wells.

At the end of this step, it should be observed that between the wells, there is no residual liquid, thus providing physical separation between each of the wells and thus avoiding any risk of cross-contamination between the hydrating supports 3. The liquid is maintained in the wells as a result of the shape and the special geometrical features that enhance retention of the liquid in the wells and as a result of the hydrophilic properties of the material constituting the container 4. This operation of distributing the liquid samples is an operation that is simple, easy to carry out properly, accurate, and without risk of overflow since the liquid remains confined inside the bowl 16 as a result of the peripheral margin 14.

Figure 17B:
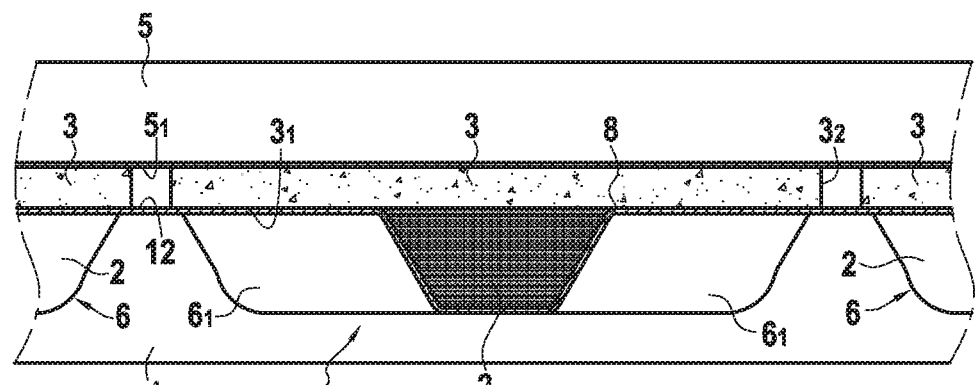
FIG. 17B is an elevation section showing the hydrating operation during which the hydrating support is placed in contact with the liquid sample.
Figure 17C:
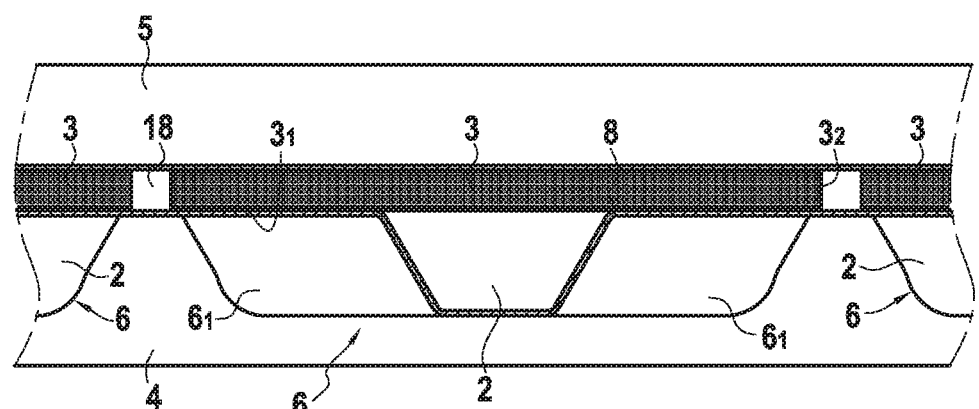
FIG. 17C is an elevation section view showing the device at the end of the operation of hydrating the hydrating support by the liquid samples.

The following step consists in positioning the lid 5 and the container 4 in a hydrating position in which each hydrating support 3 is in contact with a liquid well. For this purpose, the lid 5 and the container 4 are moved towards each other so that the hydrating supports 3 come into a position superposed over and then in contact with the peripheral rims 12 of the wells 7. In this abutment position, as shown in FIG. 17B, each hydrating support 3 is in contact via its absorption face $3_1$ with a liquid sample filling the well(s), thereby enabling each liquid sample to be absorbed by capillarity into the hydrating support placed facing it. Each liquid sample 2 contained in the well 6 is transferred by capillarity instantaneously and simultaneously for all of the hydrating supports 3 (FIG. 17C). The transfer of the liquid sample into the hydrating support 3 is performed without any liquid migration front appearing. The uniformity of the reaction medium impregnating the hydrating support 3 is thus not modified. Since the hydrating supports 3 are typically separate, any risk of cross-contamination is very limited.

The lid 5 and the container 4 are maintained in this hydrating position to enable an incubation step to be performed. With the liquid samples 2 trapped in the hydrating supports 3, incubation may be performed with the device in any position without any risk of the liquid sample running. It should be observed that the corridors 18 arranged between the hydrating supports 3 allow air to pass in order to encourage growth during incubation. Likewise, the empty wells 6 leave a volume of air available to encourage growth during incubation. Once the feed microchannels 16 are emptied, they enable air to flow inside the cavity that has been emptied of its sample. The container 4 and the lid 5 are adjusted so as to control the flow of air inside the device depending on the intended application. Provision may thus be made either to provide sealing for limiting evaporation during incubation and limiting drying of the hydrating supports, or else to provide controlled ventilation of the hydrating supports, e.g. in order to encourage microbial growth during incubation.

At the end of the incubation step, a reading step may be performed to read each hydrating support 3 in order to detect and/or identify and/or enumerate at least one target microorganism in a liquid sample that might contain it. Advantageously, this step of reading each hydrating support 3 is performed directly through the container and/or the lid, with the naked eye or by using imaging systems or using a read accessory. In another variant embodiment, it should be observed that after the incubation step, the container 4 may be replaced by a transparent or translucent flat bottom through which the operation of reading each hydrating support is performed.

The invention claimed is:

1. A device for hydrating a hydrating support with a liquid sample, the device comprising:
   a container for receiving a liquid sample, the container including a well that is upwardly open at a top edge; and
   a lid having a bottom face having the hydrating support fastened thereto, to present an absorption face for absorbing a liquid sample when the lid and the container occupy a hydrating position in which the hydrating support is in contact with the liquid sample via a hydrating interface;
   wherein the hydrating support contains a reaction medium having all of the elements necessary for the survival and/or growth of a microorganism;
   wherein the container presents, by means of the well, a calibrated volume for receiving a liquid sample;
   wherein the well presents a hydrating calibrated open section for hydrating the hydrating support defined by the top edge of the well; and
   wherein the hydrating calibrated open section comprises an area that is less than the area of the absorption face of the hydrating support, in order to control the absorption by capillarity of the liquid sample by the hydrating support.

2. The device according to claim 1, wherein the area of the calibrated open section for hydrating the hydrating support by the liquid sample defined by the well is such that the ratio of this area over the area of the absorption face of the hydrating support lies in the range 40% to 80%.

3. The device according to claim 1, wherein the container comprises a plurality of wells for a plurality of liquid samples, and wherein the lid is fitted with a plurality of hydrating supports that are spaced apart from one another by separation corridors and each of which is to be hydrated, in the hydrating position by the liquid sample.

4. The device according to claim 3, wherein the area of the calibrated open section for hydrating the plurality of hydrating supports is defined by the plurality of wells, each presenting plurality of hydrating calibrated open sections, which sections in combination with other well sections, present a total area corresponding to the area of the calibrated open section for hydrating a hydrating support.

5. The device according to claim 1, wherein the area of the calibrated open section for hydrating the hydrating support with the liquid sample is defined by the well.

6. The device according to claim 1, wherein the well includes a plurality of reception cavities for portions of the liquid sample, the reception cavities communicating with one another, at least via the hydrating calibrated open section, which has an outline that possesses lobes.

7. The device according to claim 1, wherein the well communicates with a microchannel having a portion situated outside the hydrating interface, wherein the well and the microchannel define a calibrated reception volume for receiving a liquid sample and presenting the hydrating calibrated open section defined by the top edge of the well and at least a portion of the top edge of the microchannel.

8. The device according to claim 7, wherein the well presents the hydrating calibrated open section defined by an outline that is outside the microchannel, thereby leaving a peripheral belt in the hydrating position on the absorption face of the hydrating support, which belt lies between said outline and the peripheral edge of the hydrating support.

9. The device according to claim 7, wherein the well including the microchannel defines a calibrated volume adapted so that, in the hydrating position of the lid and of the container, the liquid sample is absorbed completely by the hydrating support.

10. The device according to claim 7, wherein the well including the microchannel defines a calibrated volume adapted so that in the hydrating position of the lid and of the container, the hydrating support is completely hydrated.

11. The device according to claim 7, wherein the container includes a plate in which the well and the microchannel are arranged, so as to be surrounded by a peripheral rim that serves, in the hydrating position, as an abutment surface for the hydrating support.

12. The device according to claim 1, wherein the well presents the hydrating calibrated open section defined by an outline of shape selected in such a manner that none of the points taken inside said section is situated at a linear distance from the closest outline of said section that is greater than 4 mm.

13. The device according to claim 1, wherein the well presents the hydrating calibrated open section defined by an outline of shape that is selected in such a manner that the smallest dimension of said section is greater than 1.5 mm.

14. The device according to claim 1, wherein the well presents the hydrating calibrated open section defined by an outline of shape selected in such a manner that none of the points taken between the outside of said section and the outline of the absorption face of the hydrating support is situated at a linear distance from the closest outlines of said face or of said section that is greater than 3 mm.

15. The device according to claim 1, wherein the lid comprises a plurality of hydrating supports, each of which is to be hydrated by the liquid sample, and wherein the number and the volume of wells facing the plurality of hydrating supports are identical for each one of the plurality of hydrating supports.

16. The device according to claim 1, wherein the well presents a profile that tapers going away from its top edge.

17. The device according to claim 1, wherein the container includes a plate from which a peripheral margin surrounding the well projects upwards, defining, internally, a distribution bowl for distributing the liquid sample.

18. The device according to claim 17, wherein the lid comprises a peripheral groove suitable for engaging on the peripheral margin of the container, in order to provide engagement that is leaktight, or that includes controlled ventilation.

19. The device according to claim 1, further comprising a centering system for relative centering between the lid and the container in order to position the hydrating support in a position that is superposed relative to the well for receiving the liquid sample.

20. The device according to claim 1, further comprising a locking system for locking the lid and the container in a stable closed position corresponding to the hydrating position.

21. The device according to claim 1, wherein the container and/or the lid are made of a material that is transparent or translucent.

22. The device according to claim 1, wherein the well is provided with a stain for the liquid sample in order to assist in filling said well.

23. A method of hydrating a hydrating support with a liquid sample using the device according to claim 1, in order to detect and/or identify and/or enumerate a target microorganism in a liquid sample the method comprising the following steps:
distributing the liquid sample in the well;
positioning the lid and the container in a hydrating position in which the hydrating support is in contact with the liquid sample;
maintaining the lid and the container in the hydrating position, and carrying out an incubation step; and
reading the hydrating support in order to detect and/or identify and/or enumerate the target microorganism.

24. The method according to claim 23, comprising distributing the liquid sample by pouring the liquid sample into the container, and by agitating the container to ensure that the liquid sample completely fills the well.

25. The method according to claim 23, comprising reading the hydrating support through the container and/or the lid.

26. The method according to claim 23, further comprising, after the incubation step, replacing the container with a plane bottom that is transparent or translucent, and reading the hydrating support through the plane bottom.

* * * * *